US008979991B2

(12) United States Patent
Torabinejad et al.

(10) Patent No.: US 8,979,991 B2
(45) Date of Patent: *Mar. 17, 2015

(54) SUBSTANCES AND METHOD FOR REPLACING NATURAL TOOTH MATERIAL

(71) Applicant: Loma Linda University, Loma Linda, AE (US)

(72) Inventors: Mahmoud Torabinejad, Loma Linda, CA (US); Homayoun Moaddel, Pomona, CA (US)

(73) Assignee: Loma Linda University, Loma Linda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/825,674

(22) PCT Filed: Mar. 20, 2013

(86) PCT No.: PCT/US2013/033164
§ 371 (c)(1),
(2) Date: Mar. 22, 2013

(87) PCT Pub. No.: WO2013/142608
PCT Pub. Date: Sep. 26, 2013

(65) Prior Publication Data
US 2014/0134573 A1    May 15, 2014

Related U.S. Application Data

(60) Provisional application No. 61/768,801, filed on Feb. 25, 2013, provisional application No. 61/712,058, filed on Oct. 10, 2012, provisional application No. 61/613,797, filed on Mar. 21, 2012.

(51) Int. Cl.
*A61C 5/00* (2006.01)
*A61K 6/02* (2006.01)
*A61K 6/06* (2006.01)
*A61C 5/04* (2006.01)
*A61K 6/00* (2006.01)
*C04B 14/30* (2006.01)
*C04B 7/02* (2006.01)

(52) U.S. Cl.
CPC ............... *A61K 6/0606* (2013.01); *A61C 5/04* (2013.01); *A61K 6/0008* (2013.01); *C04B 14/30* (2013.01); *A61K 6/0038* (2013.01); *C04B 7/02* (2013.01)
USPC ............................ 106/35; 106/713; 106/816

(58) Field of Classification Search
CPC . A61K 6/0008; A61K 6/0038; A61K 6/0606; C04B 7/02; C04B 14/30
USPC .......................................... 106/35, 713, 816
See application file for complete search history.

(56) References Cited

U.S. PATENT DOCUMENTS

| | | |
|---|---|---|
| 3,973,972 A | 8/1976 | Muller |
| 4,171,544 A | 10/1979 | Hench et al. |
| 4,337,186 A | 6/1982 | Crisp et al. |
| 4,376,835 A | 3/1983 | Schmitt et al. |
| 4,557,691 A | 12/1985 | Martin et al. |
| 4,652,441 A | 3/1987 | Okada et al. |
| 5,236,362 A | 8/1993 | Cohen et al. |
| 5,415,547 A | 5/1995 | Torabinejad et al. |
| 5,769,638 A | 6/1998 | Torabinejad et al. |
| 2009/0314181 A1 | 12/2009 | Primus |
| 2010/0291512 A1 | 11/2010 | Yoo et al. |
| 2011/0104644 A1 | 5/2011 | Primus et al. |
| 2012/0156308 A1 | 6/2012 | Lovschall et al. |
| 2013/0066325 A1 | 3/2013 | Engqvist et al. |
| 2014/0162217 A1 | 6/2014 | Torabinejad et al. |

FOREIGN PATENT DOCUMENTS

| | | |
|---|---|---|
| CN | 102113965 B | 1/2013 |
| WO | WO 94/24955 | 11/1994 |
| WO | WO20040937334 A2 | 11/2004 |
| WO | WO2005087178 A1 | 9/2005 |
| WO | WO 2011/023199 * | 3/2011 |
| WO | WO2011049629 A1 | 4/2011 |

OTHER PUBLICATIONS

Loma Linda University, International Search Report & Written Opinion of the International Searching Authority, issued for International Patent Application No. PCT/US2013/33164 on Jul. 24, 2013.
Abdal et al., The Apical Seal Via the Retrosurgical Approach, Oral Surg., Aug. 1982, at pp. 213-218.
Chong et al., The Adaption and Sealing Ability of Light Cured Glass Ionomer Retrograde Root Fillings, Int. Endod. J., Sep. 1991, vol. 24, Issue 5 at pp. 223-232.
Frank J. Vertucci & Richard G. Beatty, Apical Leakage Associated with Retrofilling Techniques: A Dye Study, Journal of Endodontics, Aug. 1986, vol. 12, No. 8, at pp. 331-336.
Gandolfi et al.: Apatite-forming ability (bioactivity) of ProRoot MTA, Int. Endod. J. Oct. 2010, vol. 43, Issue 10, at pp. 917-929.
Tronstad et al., Sealing Ability of Dental Amalgams as Retrograde Fillings in Endodontic Therapy, Journal of Endodontics, Dec. 1983, vol. 9, No. 12, at pp. 551-552.
Amendment After Pre-Interview Communication dated Jul. 18, 2014, filed in U.S. Appl. No. 14/180,711 in 6 pages.

(Continued)

*Primary Examiner* — Carol M Koslow
(74) *Attorney, Agent, or Firm* — Knobbe, Martens, Olson & Bear LLP

(57) ABSTRACT

A substance that sets in a relatively short time for use in general dentistry and in endodontics to replace natural tooth material, the substance comprising untreated mineral trioxide aggregate and milled mineral trioxide aggregate, or comprising untreated mineral trioxide aggregate, milled mineral trioxide aggregate and water. A method of making a substance that sets in a relatively short time for use in general dentistry and in endodontics to replace natural tooth material, the method comprising milling by high shear and impact impingement of particles using high pressure homogenization. A method for use in general dentistry and in endodontics to replace natural tooth material.

37 Claims, No Drawings

(56) References Cited

OTHER PUBLICATIONS

First Action Interview Pilot Program Pre-Interview Communication dated on Jul. 18, 2014, received in U.S. Appl. No. 14/180,711 in 5 pages.

Gessner G. Hawley, Hawley's Condensed Chemical Dictionary (9th Ed. 1977), p. 444, with cover page, in 2 pages.

Response to Restriction Requirement dated on Jun. 2, 2014, filed in U.S. Appl. No. 14/180,711 in 2 pages.

Restriction Requirement dated Jun. 2, 2014, received in U.S. Appl. No. 14/180,711 in 7 pages.

* cited by examiner

SUBSTANCES AND METHOD FOR REPLACING NATURAL TOOTH MATERIAL

CROSS-REFERENCE TO RELATED APPLICATIONS

The present Application is a national phase of International Patent Application No. PCT/US2013/033164 titled "Substances and Method for Replacing Natural Tooth Material," filed Mar. 20, 2013, which claims the benefit of U.S. Provisional Patent Application 61/768,801, titled "Substances and Method for Replacing Natural Tooth Material," filed Feb. 25, 2013; U.S. Provisional Patent Application 61/712,058, titled "Substances and Method for Replacing Natural Tooth Material," filed Oct. 10, 2012; and U.S. Provisional Patent Application 61/613,797, titled "Substances and Method for Replacing Natural Tooth Material," filed Mar. 21, 2012; the contents of which are incorporated herein by reference in their entirety.

BACKGROUND

Mineral trioxide aggregate (MTA) (sold under the trade names gray or white ProRoot® MTA (Dentsply International Inc., York, Pa., US) is a substance currently used in general dentistry and in endodontics to replace natural tooth material in apexification, pulp capping, pulpotomy, regenerative endodontics, root canal filling, root-end filling and root perforation repair. While mineral trioxide aggregate has proven to be biocompatible and suitable for these procedures, mineral trioxide aggregate disadvantageously takes approximately three hours to set. This extended time for setting usually requires a patient to return for a second visit to complete treatment increasing the cost and inconvenience of treatment. Further disadvantageously, irrigating the operative field before the mineral trioxide aggregate has set can evacuate some of the mineral trioxide aggregate thereby requiring an additional application of mineral trioxide aggregate.

Therefore, there is a need for a substance to replace natural tooth material that is not subject to these disadvantages.

SUMMARY

According to one embodiment of the present invention, there is provided a substance for use in general dentistry and in endodontics to replace natural tooth material. The substance comprises untreated mineral trioxide aggregate and milled mineral trioxide aggregate, where the untreated mineral trioxide aggregate and milled mineral trioxide aggregate together are total mineral trioxide aggregate. In one embodiment, the substance further comprises water. In one embodiment, the untreated mineral trioxide aggregate comprises a median maximum particle diameter size of between five and thirty times larger than the median maximum particle diameter size of the milled mineral trioxide aggregate. In another embodiment, the untreated mineral trioxide aggregate comprises a median maximum particle diameter size of between five and fifteen times larger than the median maximum particle diameter size of the milled mineral trioxide aggregate. In another embodiment, the untreated mineral trioxide aggregate comprises a median maximum particle diameter size of between eight and twelve times larger than the median maximum particle diameter size of the milled mineral trioxide aggregate. In one embodiment, the substance comprises between 1% and 99.9% untreated mineral trioxide aggregate and between 0.1% and 99% milled mineral trioxide aggregate. In another embodiment, the substance comprises between 25% and 99.5% untreated mineral trioxide aggregate and between 0.5% and 75% milled mineral trioxide aggregate. In another embodiment, the substance comprises between 40% and 99% untreated mineral trioxide aggregate and between 1% and 60% milled mineral trioxide aggregate. In another embodiment, the substance comprises between 45% and 75% untreated mineral trioxide aggregate and between 25% and 55% milled mineral trioxide aggregate. In another embodiment, the substance comprises 75% untreated mineral trioxide aggregate and 25% milled mineral trioxide aggregate. In another embodiment, the substance comprises 50% untreated mineral trioxide aggregate and 50% milled mineral trioxide aggregate. In one embodiment, the substance comprises between 50% and 95% total mineral trioxide aggregate and between 5% and 50% water, where the total mineral trioxide aggregate comprises between 1% and 99.9% untreated mineral trioxide aggregate and between 0.1% and 99% milled mineral trioxide aggregate. In another embodiment, the substance comprises between 50% and 95% total mineral trioxide aggregate and between 5% and 50% water, where the total mineral trioxide aggregate comprises between 25% and 99.5% untreated mineral trioxide aggregate and between 0.5% and 75% milled mineral trioxide aggregate. In another embodiment, the substance comprises between 50% and 95% total mineral trioxide aggregate and between 5% and 50% water, where the total mineral trioxide aggregate comprises between 40% and 99% untreated mineral trioxide aggregate and between 1% and 60% milled mineral trioxide aggregate. In another embodiment, the substance comprises between 50% and 95% total mineral trioxide aggregate and between 5% and 50% water, where the total mineral trioxide aggregate comprises between 45% and 75% untreated mineral trioxide aggregate and between 25% and 55% milled mineral trioxide aggregate. In another embodiment, the substance comprises between 50% and 95% total mineral trioxide aggregate and between 5% and 50% water, where the total mineral trioxide aggregate comprises 75% untreated mineral trioxide aggregate and 25% milled mineral trioxide aggregate. In another embodiment, the substance comprises between 50% and 95% total mineral trioxide aggregate and between 5% and 50% water, where the total mineral trioxide aggregate comprises 50% untreated mineral trioxide aggregate and 50% milled mineral trioxide aggregate. In another embodiment, the substance comprises between 60% and 90% total mineral trioxide aggregate and between 10% and 40% water, where the total mineral trioxide aggregate comprises between 1% and 99.9% untreated mineral trioxide aggregate and between 0.1% and 99% milled mineral trioxide aggregate. In another embodiment, the substance comprises between 60% and 90% total mineral trioxide aggregate and between 10% and 40% water, where the total mineral trioxide aggregate comprises between 25% and 99.5% untreated mineral trioxide aggregate and between 0.5% and 75% milled mineral trioxide aggregate. In another embodiment, the substance comprises between 60% and 90% total mineral trioxide aggregate and between 10% and 40% water, where the total mineral trioxide aggregate comprises between 40% and 99% untreated mineral trioxide aggregate and between 1% and 60% milled mineral trioxide aggregate. In another embodiment, the substance comprises between 60% and 90% total mineral trioxide aggregate and between 10% and 40% water, where the total mineral trioxide aggregate comprises between 45% and 75% untreated mineral trioxide aggregate and between 25% and 55% milled mineral trioxide aggregate. In another embodiment, the substance comprises between 60% and 90% total mineral trioxide aggregate and between 10% and 40% water, where the total mineral trioxide aggregate comprises 75% untreated mineral trioxide aggregate and 25% milled mineral trioxide aggregate. In another embodiment, the substance comprises between 60% and 90% total mineral trioxide aggregate and between 10% and 40% water, where the total mineral trioxide aggregate comprises 50% untreated mineral trioxide aggregate and 50% milled mineral trioxide aggregate. In another embodiment, the substance comprises between 70% and 80% total mineral trioxide aggregate and between 20% and 30% water, where the total mineral trioxide aggregate comprises between 1% and 99.9% untreated mineral trioxide aggregate and between 0.1% and 99% milled mineral trioxide aggregate. In another embodiment, the substance comprises between 70% and 80% total mineral trioxide aggregate and between 20% and 30% water, where the total mineral trioxide aggregate comprises between 25% and 99.5% untreated mineral trioxide aggregate and between 0.5% and 75% milled mineral trioxide aggregate. In another embodiment, the substance comprises between 70% and 80% total mineral trioxide aggregate and between 20% and 30% water, where the total mineral trioxide aggregate comprises between 40% and 99% untreated mineral trioxide aggregate and between 1% and 60% milled mineral trioxide aggregate. In another embodiment, the substance comprises between 70% and 80% total mineral trioxide aggregate and between 20% and 30% water, where the total mineral trioxide aggregate comprises between 45% and 75% untreated mineral trioxide aggregate and between 25% and 55% milled mineral trioxide aggregate. In another embodiment, the substance comprises between 70% and 80% total mineral trioxide aggregate and between 20% and 30% water, where the total mineral trioxide aggregate comprises 75% untreated mineral trioxide aggregate and 25% milled mineral trioxide aggregate. In another embodiment, the substance comprises between 70% and 80% total mineral trioxide aggregate and between 20% and 30% water, where the total mineral trioxide aggregate comprises 50% untreated mineral trioxide aggregate and 50% milled mineral trioxide aggregate. In another embodiment, the substance comprises 75% total mineral trioxide aggregate and 25% water, where the total mineral trioxide aggregate comprises 75% untreated mineral trioxide aggregate and 25% milled mineral trioxide aggregate. In another embodiment, the substance comprises 75% total mineral trioxide aggregate and 25% water, where the total mineral trioxide aggregate comprises 50% untreated mineral trioxide aggregate and 50% milled mineral trioxide aggregate.

According to another embodiment of the present invention, there is provided a method for use in general dentistry and in endodontics to replace natural tooth material. The method comprises: a) performing a dental procedure; b) providing a substance according to the present invention; c) using the substance to fill a space in the tooth; and d) allowing the substance to set. In one embodiment, the dental procedure is an endodontic procedure. In another embodiment, the dental procedure comprises removing part of the natural tooth material of a tooth. In another embodiment, the dental procedure comprises removing material that replaced natural tooth material. In another embodiment, the dental procedure is selected from the group consisting of apexification, pulp capping, pulpotomy, regenerative endodontics, root canal filling, root-end filling, root perforation repair and sealer during filling or root canals.

According to another embodiment of the present invention, there is provided a method of making a substance for use in general dentistry and in endodontics to replace natural tooth material, where the substance sets in a relatively short time. The method comprises: a) selecting a material suitable for use in the method to make a substance for use in general dentistry and in endodontics to replace natural tooth material, where the material comprises particles having a median maximum particle diameter; b) mixing the selected material with a non-aqueous liquid creating a mixture of the material and liquid; c) providing an instrument for milling by high shear and impact impingement of particles using high pressure homogenization; d) placing the mixture of material and liquid into the instrument for milling by high shear and impact impingement of particles using high pressure homogenization; and e) actuating the instrument thereby milling the material within the mixture, thereby reducing the median maximum particle diameter, and thereby making the substance for use in general dentistry and in endodontics to replace natural tooth material. In one embodiment, the material is mineral trioxide aggregate. In one embodiment, the liquid is selected from the group consisting of methanol, ethanol and isopropanol. In a preferred embodiment, the liquid is ethanol. In one embodiment, the material is mixed with the liquid in a ratio of between 1 part material to between 1 and 100 parts liquid. In another embodiment, the material is mixed with the liquid in a ratio of between 1 part material to between 1 and 20 parts liquid. In another embodiment, the material is mixed with the liquid in a ratio of between 1 part material to between 5 and 20 parts liquid. In another embodiment, the material is mixed with the liquid in a ratio of between 1 part material to between 5 and 10 parts liquid. In another embodiment, the material is mixed with the liquid in a ratio of 1 part material to 9 parts liquid. In one embodiment, mixing the material with a liquid comprises using a magnetic stir bar to produce a suspension. In one embodiment, placing the mixture of material and liquid into the instrument comprises pouring the mixture into a reservoir of the instrument. In one embodiment, the reservoir comprises a device for preventing premature settling of the mixture which would cause a concentration gradient within the instrument or a part of the instrument, and the method further comprises actuating the device to prevent premature settling of the mixture which would cause a concentration gradient within the instrument or a part of the instrument. In one embodiment, the device is an overhead propeller. In another embodiment, milling the material within the mixture comprises cycling the instrument between two and one hundred cycles. In another embodiment, milling the material within the mixture comprises cycling the instrument between two and fifty cycles. In another embodiment, milling the material within the mixture comprises cycling the instrument between two and thirty cycles. In another embodiment, milling the material within the mixture comprises cycling the instrument between five and thirty cycles. In another embodiment, milling the material within the mixture comprises is using a pressure between 1000 to 70,000 psi. In another embodiment, milling the material within the mixture comprises is using a pressure of 30,000 psi. In another embodiment, the method further comprises evaporating the liquid from the milled material. In another embodiment, the method further comprises collecting the milled material after milling the material. According to another embodiment of the present invention, there is provided a substance made according to the method of the present invention.

DESCRIPTION

According to one embodiment of the present invention, there is provided a substance that sets in a relatively short time for use in general dentistry and in endodontics to replace natural tooth material. In one embodiment, the substance comprises untreated mineral trioxide aggregate and milled mineral trioxide aggregate (prepared by high shear and impact impingement of particles using high pressure homogenization). In a preferred embodiment, the substance comprises untreated mineral trioxide aggregate, milled mineral trioxide aggregate and water. According to another embodiment of the present invention, there is provided a method of making a substance that sets in a relatively short time for use in general dentistry and in endodontics to replace natural tooth material. According to another embodiment of the present invention, there is provided a substance made according to the present method. According to another embodiment of the present invention, there is provided a method for use in general dentistry and in endodontics to replace natural tooth material. In one embodiment, the method comprises providing a substance according to the present invention. The substances and method will now be disclosed in detail.

As used in this disclosure, except where the context requires otherwise, the term "comprise" and variations of the term, such as "comprising," "comprises" and "comprised" are not intended to exclude other additives, components, integers or steps.

As used in this disclosure, except where the context requires otherwise, the method steps disclosed are not intended to be limiting nor are they intended to indicate that each step is essential to the method or that each step must occur in the order disclosed.

As used in this disclosure, except where indicated otherwise, "mineral trioxide aggregate," and "untreated mineral trioxide aggregate," mean the substance generally sold under the trade name gray or white ProRoot® MTA (Dentsply International Inc., York, Pa., US). As will be understood by those with skill in the art with respect to this disclosure, before mixing with liquid to cause the untreated mineral trioxide aggregate to set, mineral trioxide aggregate is mixture of a refined Portland cement and bismuth oxide, and generally comprises a mixture of bismuth oxide, dicalcium silicate, tetracalcium aluminoferrite, tricalcium aluminate and tricalcium silicate. Additionally, "mineral trioxide aggregate," and "untreated mineral trioxide aggregate," also mean the substance generally sold under the trade name white ProRoot® MTA (Dentsply International Inc., York, Pa., US), which is similar in composition to gray ProRoot® MTA except that white ProRoot® MTA lacks tetracalcium alumino-ferrite.

Unless specified otherwise, all ratios given in this disclosure are by weight.

As used in this disclosure, "relatively short time" means between five minutes and twenty minutes, a clinically desirable setting time for substances that replace natural tooth material.

As used in this disclosure, "median maximum particle diameter size" means that 50% of the sample has a smaller maximum particle diameter and 50% of the sample has a larger maximum particle diameter.

As used in this disclosure, "milled" in reference to substances and methods of the present invention means "impingement of particles at high shear rate and impact by high pressure homogenization."

According to one embodiment of the present invention, there is provided a substance for use in general dentistry and in endodontics to replace natural tooth material. The substance sets within a tooth in a relatively short time, minutes rather than hours as is usual for currently used substances. In one embodiment, the substance comprises untreated mineral trioxide aggregate and milled mineral trioxide aggregate (prepared by high shear and impact impingement of particles using high pressure homogenization). In a preferred embodiment, the substance comprises untreated mineral trioxide aggregate, milled mineral trioxide aggregate and water. Mineral trioxide aggregate as currently used, such as sold under the trade name gray or white ProRoot® MTA (Dentsply International Inc., York, Pa., US), was tested to determine the maximum particle diameter size of the mineral trioxide aggregate particles before contacting with liquid for setting. Mineral trioxide aggregate particles (hereinafter referred to as "untreated mineral trioxide aggregate") were found to have a maximum particle diameter of between 0.7 and 42.2 microns with a median of 3.5 microns and a standard deviation of 4.1 microns. A study was performed to determine the effect of adding mineral trioxide aggregate that had been milled by high shear and impact impingement of particles using high pressure homogenization (hereinafter referred to as "milled mineral trioxide aggregate" in the context of the present invention) to the setting time of untreated mineral trioxide aggregate, where milling the mineral trioxide aggregate reduced the maximum particle diameter to between 0.16 and 2.45 microns with a median of 0.49 microns, and a standard deviation of 0.5 microns. That is, the untreated mineral trioxide aggregate had a median maximum particle diameter size approximately eight times the median maximum particle diameter size of the milled mineral trioxide aggregate. The study was performed following ISO standard 6876: 1986 for dental materials which specifies the requirements for dental materials used as filling materials. The milled mineral trioxide aggregate was prepared as follows. First, untreated mineral trioxide aggregate (gray ProRoot® MTA) was obtained from Dentsply International Inc. (York, Pa., US). The starting median particle size for the untreated mineral trioxide aggregate was determined to be 3.8 microns. The untreated mineral trioxide aggregate was mixed with ethanol in a ratio of 1 to 9 by weight using a magnetic stir bar to produce a suspension. The suspension was poured into the reservoir of an M-110EH Microfluidizer® (Microfluidics, Newton, Mass., US) with an overhead propeller mixer also in the reservoir (to prevent premature settling causing a concentration gradient in the check-valve of the processor due to the high density of mineral trioxide aggregate). The suspension was forced at extreme high pressure through a very small diamond orifice. The high pressures (up to 40,000 psi/) used delivers the product into the interaction chamber using a constant pressure pumping system. Precisely engineered microchannels within the chamber range from 50-500 microns and generate unsurpassed shear and impact forces that cause homogenization and de-agglomerates the mineral trioxide aggregate particles. The temperature was regulated by a heat exchanger, and the lack of moving parts maximizes uptime. The use of M-110EH Microfluidizer® equipment forced the entire dispersion through the same tortuous path, and as a result, produced tighter/smaller particle size distributions than other technologies. It also creates a narrower particle size distribution. Next, the suspension was milled for between five and thirty cycles in a G10Z (87 microns) diamond Interaction Chamber (IXC) at 30,000 psi and the maximum particle diameter size was measured during the cycles. In general, the suspension can be milled for between two and one hundred cycles. Further in general, the suspension can be milled at pressure between 1000 to 70,000. The median maximum particle diameter size of the untreated mineral trioxide aggregate was reduced to 0.49 microns after fifty passes, thereby producing the milled mineral trioxide aggregate, or approximately an eight-fold reduction in median particle size. Next, the ethanol was evaporated off in an oven at 65° C. and the solids were collected for analysis of the effects of adding the milled mineral trioxide aggregate to untreated mineral trioxide aggregate to the setting time of untreated mineral trioxide aggregate.

Referring now to Table 1, there are shown the results of this study.

TABLE 1

| Untreated Mineral Trioxide Aggregate to Milled Mineral Trioxide Aggregate* | Setting Time Sample #1 | Setting Time Sample #2 | Setting Time Sample #3 | Average Setting Time |
|---|---|---|---|---|
| 100%/0% | 02:25:55 | 02:26:11 | 03:12:00 | 02:41:22 |
| 75%/25% | 00:11:52 | 00:12:30 | 00:14:30 | 00:12:57 |
| 50%/50% | 00:06:45 | 00:07:05 | 00:06:30 | 00:06:47 |
| 0%/100% | 00:06:33 | 00:06:33 | 00:06:33 | 00:06:33 |

*All tests were done using a ratio of three parts solids (milled mineral trioxide aggregate and untreated mineral trioxide aggregate) to one part distilled water (600 mg solids/200 liquid).

As can be seen, combining 75% or 50% with untreated mineral trioxide aggregate (comprising a maximum particle diameter of between 0.7 and 42.2 microns with a median of 3.8 microns) with 25% or 50%, respectively, milled mineral trioxide aggregate (comprising a maximum particle diameter of between 0.16 and 2.45 microns with a median of 0.49 microns), and then mixing the combination with one part water to three parts (combined mineral trioxide aggregate) by weight reduced setting time from hours to between approximately six and fourteen minutes. Using one part water with three parts 100% milled mineral trioxide aggregate by weight also reduced the setting time to between six to seven minutes similar to the reduction achieved with the combination of 50% milled mineral trioxide aggregate and 50% untreated mineral trioxide aggregate in water; however, as there are costs associated with milling mineral trioxide aggregate and no apparent advantages with respect to setting time for increasing the amount of milled mineral trioxide aggregate in the substance, it is preferred to use the minimum amount of milled mineral trioxide aggregate in the substance suitable for reducing setting time to a clinically acceptable amount as will be understood by those with skill in the art with respect to this disclosure. Further, because distilled water is non-toxic in the clinical setting, inexpensive and readily available, distilled water is preferred as the mineral trioxide aggregate combination solvent for the substance of the present invention.

In one embodiment, the substance according to the present invention comprises untreated mineral trioxide aggregate and milled mineral trioxide aggregate by high pressure homogenization. In one embodiment, the untreated mineral trioxide aggregate comprises a median maximum particle diameter size of between five and twelve times larger than the median maximum particle diameter size of the milled mineral trioxide aggregate. In another embodiment, the untreated mineral trioxide aggregate comprises a median maximum particle diameter size of between five and ten times larger than the median maximum particle diameter size of the milled mineral trioxide aggregate. In another embodiment, the untreated mineral trioxide aggregate comprises a median maximum particle diameter size of between seven and eight times larger than the median maximum particle diameter size of the milled mineral trioxide aggregate.

According to another embodiment of the present invention, there is provided a substance for use in general dentistry and in endodontics to replace natural tooth material. The substance sets within a tooth in a relatively short time, minutes rather than hours. In one embodiment, the substance comprises a combination of milled mineral trioxide aggregate, untreated mineral trioxide aggregate and a liquid. In one embodiment, the liquid is water. In a preferred embodiment, the water is distilled water. In one embodiment, the water is selected from the group consisting of deionized water, filtered water, slurry water and tap water. In another embodiment, the liquid is a local anesthetic, such as for example lidocaine hydrochloride, with or without epinephrine bitartrate. Other local anesthetic can also be used, as will be understood by those with skill in the art with respect to this disclosure.

In one embodiment, the substance comprises between 50% and 95% total mineral trioxide aggregate and between 5% and 50% water, where the total mineral trioxide aggregate comprises between 1% and 99.9% untreated mineral trioxide aggregate and between 0.1% and 99% milled mineral trioxide aggregate. In another embodiment, the substance comprises between 50% and 95% total mineral trioxide aggregate and between 5% and 50% water, where the total mineral trioxide aggregate comprises between 25% and 99.5% untreated mineral trioxide aggregate and between 0.5% and 75% milled mineral trioxide aggregate. In one embodiment, the substance comprises between 50% and 95% total mineral trioxide aggregate and between 5% and 50% water, where the total mineral trioxide aggregate comprises between 40% and 99% untreated mineral trioxide aggregate and between 1% and 60% milled mineral trioxide aggregate. In one embodiment, the substance comprises between 50% and 95% total mineral trioxide aggregate and between 5% and 50% water, where the total mineral trioxide aggregate comprises between 45% and 75% untreated mineral trioxide aggregate and between 25% and 55% milled mineral trioxide aggregate. In one embodiment, the substance comprises between 50% and 95% total mineral trioxide aggregate and between 5% and 50% water, where the total mineral trioxide aggregate comprises 75% untreated mineral trioxide aggregate and 25% milled mineral trioxide aggregate. In one embodiment, the substance comprises between 50% and 95% total mineral trioxide aggregate and between 5% and 50% water, where the total mineral trioxide aggregate comprises 50% untreated mineral trioxide aggregate and 50% milled mineral trioxide aggregate.

In one embodiment, the substance comprises between 60% and 90% total mineral trioxide aggregate and between 10% and 40% water, where the total mineral trioxide aggregate comprises between 1% and 99.9% untreated mineral trioxide aggregate and between 0.1% and 99% milled mineral trioxide aggregate. In another embodiment, the substance comprises between 60% and 90% total mineral trioxide aggregate and between 10% and 40% water, where the total mineral trioxide aggregate comprises between 25% and 99.5% untreated mineral trioxide aggregate and between 0.5% and 75% milled mineral trioxide aggregate. In one embodiment, the substance comprises between 60% and 90% total mineral trioxide aggregate and between 10% and 40% water, where the total mineral trioxide aggregate comprises between 40% and 99% untreated mineral trioxide aggregate and between 1% and 60% milled mineral trioxide aggregate. In one embodiment, the substance comprises between 60% and 90% total mineral trioxide aggregate and between 10% and 40% water, where the total mineral trioxide aggregate comprises between 45% and 75% untreated mineral trioxide aggregate and between 25% and 55% milled mineral trioxide aggregate. In one embodiment, the substance comprises between 60% and 90% total mineral trioxide aggregate and between 10% and 40% water, where the total mineral trioxide aggregate comprises 75% untreated mineral trioxide aggregate and 25% milled mineral trioxide aggregate. In one embodiment, the substance comprises between 60% and 90% total mineral trioxide aggregate and between 10% and 40% water, where the total mineral trioxide aggregate comprises 50% untreated mineral trioxide aggregate and 50% milled mineral trioxide aggregate.

In one embodiment, the substance comprises between 70% and 80% total mineral trioxide aggregate and between 20% and 30% water, where the total mineral trioxide aggregate comprises between 1% and 99.9% untreated mineral trioxide aggregate and between 0.1% and 99% milled mineral trioxide aggregate. In another embodiment, the substance comprises between 70% and 80% total mineral trioxide aggregate and between 20% and 30% water, where the total mineral trioxide aggregate comprises between 25% and 99.5% untreated mineral trioxide aggregate and between 0.5% and 75% milled mineral trioxide aggregate. In one embodiment, the substance comprises between 70% and 80% total mineral trioxide aggregate and between 20% and 30% water, where the total mineral trioxide aggregate comprises between 40% and 99% untreated mineral trioxide aggregate and between 1% and 60% milled mineral trioxide aggregate. In one embodiment, the substance comprises between 70% and 80% total mineral trioxide aggregate and between 20% and 30% water, where the total mineral trioxide aggregate comprises between 45% and 75% untreated mineral trioxide aggregate and between 25% and 55% milled mineral trioxide aggregate. In one embodiment, the substance comprises between 70% and 80% total mineral trioxide aggregate and between 20% and 30% water, where the total mineral trioxide aggregate comprises 75% untreated mineral trioxide aggregate and 25% milled mineral trioxide aggregate. In one embodiment, the substance comprises between 70% and 80% total mineral trioxide aggregate and between 20% and 30% water, where the total mineral trioxide aggregate comprises 50% untreated mineral trioxide aggregate and 50% milled mineral trioxide aggregate.

In one embodiment, the substance comprises 75% total mineral trioxide aggregate and 25% water, where the total mineral trioxide aggregate comprises 75% untreated mineral trioxide aggregate and 25% milled mineral trioxide aggregate. In one embodiment, the substance comprises 75% total mineral trioxide aggregate and 25% water, where the total mineral trioxide aggregate comprises 50% untreated mineral trioxide aggregate and 50% milled mineral trioxide aggregate.

According to another embodiment of the present invention, there is provided a method of making a substance for use in general dentistry and in endodontics to replace natural tooth material, where the substance sets in a relatively short time, minutes as compared to hours. The method comprises milling by high shear and impact impingement of particles using high pressure homogenization to reduce particle size thereby producing milled particles, rather than ball milling as is currently generally used. Ball milling comprises contacting the particles to be reduced in size with a grinding media in a chamber, where the grinding media is different in composition from the particles, and where repeated contact with the grinding media reduces the size of the particles, thereby producing milled particles. The grinding media is frequently one or more than one ball, such as for example one or more than one glass ball, from which the method is named. By contrast, milling by high shear and impact impingement of particles using high pressure homogenization according to the present invention comprises forcing particles through a channel using pressure, where repeated contact of the particles to be reduced in size with each other and with the pressure and the channel walls reduces the size of the particles, thereby producing milled particles. While milling by high shear and impact impingement of particles using high pressure homogenization has been used in other fields, it has never been used in connection with the preparation of substances for use in general dentistry and in endodontics to replace natural tooth material. Further, the method of milling by high shear and impact impingement of particles using high pressure homogenization according to the present invention produces milled particles that have unexpected advantages over all other used methods, in particular decreasing the setting time of the milled particles, as disclosed in this disclosure, when the milled particles are used by themselves or when the milled particles are combined with unmilled particles in general dentistry and in endodontics to replace natural tooth material. Additionally, milling by high shear and impact impingement of particles using high pressure homogenization takes less time to reduce particle size than ball milling. Further, pieces of the grinding media used in ball milling can contaminate the milled particles produced as the grinding media wears, while the method of milling by high shear and impact impingement of particles using high pressure homogenization does not use a grinding media that can contaminate the milled particles produced. Additionally, the particle size reduction of the milled particles produced by ball milling is less uniform than the particle size reduction of the milled particles produced by milling by high shear and impact impingement of particles using high pressure homogenization, and the decreased uniformity of the milled particles produced by ball milling increases their setting time as compared with the setting time for milled particles produced by milling by high shear and impact impingement of particles using high pressure homogenization that have a more uniform size. Further, the particle size of the milled particles produced by ball milling is generally larger than the particle size of the milled particles produced by milling by high shear and impact impingement of particles using high pressure homogenization, and the larger particle size of the milled particles produced by ball milling increases their setting time as compared with the setting time for milled particles that have a smaller particle size produced by milling by high shear and impact impingement of particles using high pressure homogenization. Additionally, instruments used in ball milling are more difficult to clean in preparation for reuse than instruments used in milling by high shear and impact impingement of particles using high pressure homogenization according to the present invention, because in ball milling the milled particles must be separated from the grinding media, where in milling by high shear and impact impingement of particles using high pressure homogenization, the milled particles are merely flushed out of the instrument as there is no grinding media. Because of these advantages, milling by high shear and impact impingement of particles using high pressure homogenization is more efficient and cost effective than ball milling for making a substance for use in general dentistry and in endodontics to replace natural tooth material.

As disclosed above, the method of making a substance for use in general dentistry and in endodontics to replace natural tooth material, where the substance sets in a relatively short time, minutes as compared to hours, comprises milling by high shear and impact impingement of particles using high pressure homogenization to reduce particle size thereby producing milled particles. The method comprises, first, selecting a material suitable for use in the method to make a substance for use in general dentistry and in endodontics to replace natural tooth material, where the material comprises particles having a median maximum particle diameter. In one embodiment, the material is mineral trioxide aggregate, such as for example mineral trioxide aggregate (gray ProRoot® MTA, Dentsply International Inc., York, Pa., US).

Next, the method comprises mixing the selected material with a liquid creating a mixture of the material and liquid. Water is generally used in milling by high shear and impact impingement of particles using high pressure homogenization, however, water cannot be used in the present method because it would cause the material to set prematurely. Therefore, the liquid must be non-aqueous. In one embodiment, the liquid is an alcohol, though any suitable non-aqueous liquid can be used as will be understood by those with skill in the art with respect to this disclosure. In one embodiment, the liquid is selected from the group consisting of methanol, ethanol and isopropanol. In a preferred embodiment, the liquid is ethanol. In one embodiment, the material is mixed with the liquid in a ratio of between 1 part material to between 1 and 100 parts liquid. In one embodiment, the material is mixed with the liquid in a ratio of between 1 part material to between 1 and 20 parts liquid. In one embodiment, the material is mixed with the liquid in a ratio of between 1 part material to between 5 and 20 parts liquid. In one embodiment, the material is mixed with the liquid in a ratio of between 1 part material to between 5 and 10 parts liquid. In one embodiment, the material is mixed with the liquid in a ratio of 1 part material to 9 parts liquid. In a preferred embodiment, mixing the material with a liquid comprises using a magnetic stir bar to produce a suspension.

Then, the method comprises providing an instrument for milling by high shear and impact impingement of particles using high pressure homogenization. In one embodiment, the instrument provided is an M-110EH Microfluidizer® (Microfluidics, Newton, Mass., US), though any suitable instrument for milling by high shear and impact impingement of particles using high pressure homogenization can be used, as will be understood by those with skill in the art with respect to this disclosure.

Next, the method comprises placing the mixture of material and liquid into the instrument for milling by high shear and impact impingement of particles using high pressure homogenization. In one embodiment, placing the mixture of material and liquid into the instrument comprises pouring the mixture into a reservoir of the instrument. In a preferred embodiment, the reservoir comprises a device for preventing premature settling of the mixture which would cause a concentration gradient within the instrument or a part of the instrument, and the method further comprises actuating the device to prevent premature settling of the mixture which would cause a concentration gradient within the instrument or a part of the instrument. In one embodiment, the device is an overhead propeller.

Then, the method comprises actuating the instrument thereby milling the material within the mixture, thereby reducing the median maximum particle diameter, and thereby making the substance for use in general dentistry and in endodontics to replace natural tooth material. In one embodiment, milling the material within the mixture comprises cycling the instrument between two and one hundred cycles. In one embodiment, milling the material within the mixture comprises cycling the instrument between two and fifty cycles. In one embodiment, milling the material within the mixture comprises cycling the instrument between two and thirty cycles. In one embodiment, milling the material within the mixture comprises cycling the instrument between five and thirty cycles. In one embodiment, milling the material is performed at a pressure between 1000 to 70,000 psi. In one embodiment, milling the material is performed at a pressure of 30,000 psi. In one embodiment, the method further comprises evaporating the liquid from the milled material. For example, in one embodiment, the liquid is ethanol, and evaporating the liquid from the milled material comprises placing the milled material and liquid in an oven at 65° C. for sufficient time to evaporate the ethanol. In one embodiment, the method further comprises collecting the milled material after milling the material.

According to another embodiment of the present invention, there is provided a substance made according to the present method. In one embodiment, the substance is a substance according to the present invention.

According to another embodiment of the present invention, there is provided a method for use in general dentistry and in endodontics to replace natural tooth material. The method comprises, first performing a dental procedure. In one embodiment, the dental procedure is an endodontic procedure. In one embodiment, the dental procedure comprises removing part of the natural tooth material of a tooth. In another embodiment, the dental procedure comprises removing material that replaced natural tooth material. In a preferred embodiment, the dental procedure is selected from the group consisting of apexification, pulp capping, pulpotomy, regenerative endodontics, root canal filling, root-end filling, root perforation repair and sealer during filling or root canals. Next, the method comprises providing a substance according to the present invention. Then, the method comprises using the substance to fill a space in the tooth, and allowing the substance to set.

Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference in their entirety.

What is claimed is:

1. A substance for use in general dentistry and in endodontics to replace natural tooth material, the substance comprising:
    untreated mineral trioxide aggregate comprising particles with a median maximum particle diameter; and
    reduced particle size mineral trioxide aggregate comprising particles of mineral trioxide aggregate subjected to high shear homogenization,
    wherein the reduced particle size mineral trioxide aggregate has a reduced median maximum particle diameter compared to the particles of the untreated mineral trioxide aggregate,
    wherein the untreated mineral trioxide aggregate and reduced particle size mineral trioxide aggregate together are total mineral trioxide aggregate.

2. The substance of claim 1, further comprising a liquid selected from the group consisting of a local anesthetic and water.

3. The substance of claim 1, where the untreated mineral trioxide aggregate comprises a median maximum particle diameter size of between five and thirty times larger than the median maximum particle diameter size of the reduced particle size mineral trioxide aggregate.

4. The substance of claim 1, where the untreated mineral trioxide aggregate comprises a median maximum particle diameter size of between five and fifteen times larger than the median maximum particle diameter size of the reduced particle size mineral trioxide aggregate.

5. The substance of claim 1, where the untreated mineral trioxide aggregate comprises a median maximum particle diameter size of between eight and twelve times larger than the median maximum particle diameter size of the reduced particle size mineral trioxide aggregate.

6. The substance of claim 1, comprising between 1% and 99.9% untreated mineral trioxide aggregate and between 0.1% and 99% reduced particle size mineral trioxide aggregate.

7. The substance of claim 1, comprising between 25% and 99.5% untreated mineral trioxide aggregate and between 0.5% and 75% reduced particle size mineral trioxide aggregate.

8. The substance of claim 1, comprising between 40% and 99% untreated mineral trioxide aggregate and between 1% and 60% reduced particle size mineral trioxide aggregate.

9. The substance of claim 1, comprising between 45% and 75% untreated mineral trioxide aggregate and between 25% and 55% reduced particle size mineral trioxide aggregate.

10. The substance of claim 1, comprising 75% untreated mineral trioxide aggregate and 25% reduced particle size mineral trioxide aggregate.

11. The substance of claim 1, comprising 50% untreated mineral trioxide aggregate and 50% reduced particle size mineral trioxide aggregate.

12. The substance of claim 2, comprising between 50% and 95% total mineral trioxide aggregate and between 5% and 50% water, where the total mineral trioxide aggregate comprises between 1% and 99.9% untreated mineral trioxide aggregate and between 0.1% and 99% reduced particle size mineral trioxide aggregate.

13. The substance of claim 2, comprising between 50% and 95% total mineral trioxide aggregate and between 5% and 50% water, where the total mineral trioxide aggregate comprises between 25% and 99.5% untreated mineral trioxide aggregate and between 0.5% and 75% reduced particle size mineral trioxide are ate.

14. The substance of claim 2, comprising between 50% and 95% total mineral trioxide aggregate and between 5% and 50% water, where the total mineral trioxide aggregate comprises between 40% and 99% untreated mineral trioxide aggregate and between 1% and 60% reduced particle size mineral trioxide aggregate.

15. The substance of claim 2, comprising between 50% and 95% total mineral trioxide aggregate and between 5% and 50% water, where the total mineral trioxide aggregate comprises between 45% and 75% untreated mineral trioxide aggregate and between 25% and 55% reduced particle size mineral trioxide aggregate.

16. The substance of claim 2, comprising between 50% and 95% total mineral trioxide aggregate and between 5% and 50% water, where the total mineral trioxide aggregate comprises 75% untreated mineral trioxide aggregate and 25% reduced particle size mineral trioxide aggregate.

17. The substance of claim 2, comprising between 50% and 95% total mineral trioxide aggregate and between 5% and 50% water, where the total mineral trioxide aggregate comprises 50% untreated mineral trioxide aggregate and 50% reduced particle size mineral trioxide aggregate.

18. The substance of claim 2, comprising between 60% and 90% total mineral trioxide aggregate and between 10% and 40% water, where the total mineral trioxide aggregate comprises between 1% and 99.9% untreated mineral trioxide aggregate and between 0.1% and 99% reduced particle size mineral trioxide aggregate.

19. The substance of claim 2, comprising between 60% and 90% total mineral trioxide aggregate and between 10% and 40% water, where the total mineral trioxide aggregate comprises between 25% and 99.5% untreated mineral trioxide aggregate and between 0.5% and 75% reduced particle size mineral trioxide aggregate.

20. The substance of claim 2, comprising between 60% and 90% total mineral trioxide aggregate and between 10% and 40% water, where the total mineral trioxide aggregate comprises between 40% and 99% untreated mineral trioxide aggregate and between 1% and 60% reduced particle size mineral trioxide aggregate.

21. The substance of claim 2, comprising between 60% and 90% total mineral trioxide aggregate and between 10% and 40% water, where the total mineral trioxide aggregate comprises between 45% and 75% untreated mineral trioxide aggregate and between 25% and 55% reduced particle size mineral trioxide aggregate.

22. The substance of claim 2, comprising between 60% and 90% total mineral trioxide aggregate and between 10% and 40% water, where the total mineral trioxide aggregate comprises 75% untreated mineral trioxide aggregate and 25% reduced particle size mineral trioxide aggregate.

23. The substance of claim 2, comprising between 60% and 90% total mineral trioxide aggregate and between 10% and 40% water, where the total mineral trioxide aggregate comprises 50% untreated mineral trioxide aggregate and 50% reduced particle size mineral trioxide aggregate.

24. The substance of claim 2, comprising between 70% and 80% total mineral trioxide aggregate and between 20% and 30% water, where the total mineral trioxide aggregate comprises between 1% and 99.9% untreated mineral trioxide aggregate and between 0.1% and 99% reduced particle size mineral trioxide aggregate.

25. The substance of claim 2, comprising between 70% and 80% total mineral trioxide aggregate and between 20% and 30% water, where the total mineral trioxide aggregate comprises between 25% and 99.5% untreated mineral trioxide aggregate and between 0.5% and 75% reduced particle size mineral trioxide aggregate.

26. The substance of claim 2, comprising between 70% and 80% total mineral trioxide aggregate and between 20% and 30% water, where the total mineral trioxide aggregate comprises between 40% and 99% untreated mineral trioxide aggregate and between 1% and 60% reduced particle size mineral trioxide aggregate.

27. The substance of claim 2, comprising between 70% and 80% total mineral trioxide aggregate and between 20% and 30% water, where the total mineral trioxide aggregate comprises between 45% and 75% untreated mineral trioxide aggregate and between 25% and 55% reduced particle size mineral trioxide aggregate.

28. The substance of claim 2, comprising between 70% and 80% total mineral trioxide aggregate and between 20% and 30% water, where the total mineral trioxide aggregate comprises 75% untreated mineral trioxide aggregate and 25% reduced particle size mineral trioxide aggregate.

29. The substance of claim 2, comprising between 70% and 80% total mineral trioxide aggregate and between 20% and 30% water, where the total mineral trioxide aggregate comprises 50% untreated mineral trioxide aggregate and 50% reduced particle size mineral trioxide aggregate.

30. The substance of claim 2, comprising 75% total mineral trioxide aggregate and 25% water, where the total mineral trioxide aggregate comprises 75% untreated mineral trioxide aggregate and 25% reduced particle size mineral trioxide aggregate.

31. The substance of claim 2, comprising 75% total mineral trioxide aggregate and 25% water, where the total mineral trioxide aggregate comprises 50% untreated mineral trioxide aggregate and 50% reduced particle size mineral trioxide aggregate.

32. The substance of claim 1, wherein the reduced particle size mineral trioxide aggregate is homogenized by high shear and impact impingement of particles without the use of grinding media.

33. The substance of claim 1, wherein the total mineral trioxide aggregate sets in between five to twenty minutes when mixed with a liquid to produce a dental substance for use in general dentistry and in endodontics to replace natural tooth material.

34. The substance of claim 1, wherein only a non-aqueous liquid is used in homogenizing the reduced particle size mineral trioxide aggregate.

35. The substance of claim 34, wherein the non-aqueous liquid comprises alcohol.

36. The substance of claim 1, wherein:
the untreated mineral trioxide aggregate comprises particles with a maximum particle diameter of between about 0.7 and about 42.2 microns, with a median maximum particle diameter of about 3.8 microns, and with a standard deviation of maximum particle diameter of about 4.1 microns; and
the reduced particle size mineral trioxide are ate comprises particles with a maximum particle diameter of between about 0.16 and about 2.45 microns, with a median maximum particle diameter of about 0.49 microns, and with a standard deviation of maximum particle diameter of about 0.5 microns.

37. The substance of claim 1, wherein the total mineral trioxide aggregate comprises bismuth oxide, dicalcium silicate, tricalcium aluminate, and tricalcium silicate, and optionally comprises tetracalcium alumino-ferrite.

* * * * *

UNITED STATES PATENT AND TRADEMARK OFFICE
CERTIFICATE OF CORRECTION

Page 1 of 1

PATENT NO.        : 8,979,991 B2
APPLICATION NO.   : 13/825674
DATED             : March 17, 2015
INVENTOR(S)       : Mahmoud Torabinejad It is certified that error appears in the above-identified patent and that said Letters Patent is hereby corrected as shown below:

Title Page (item 71, Applicant) at line 2, Change "AE" for Loma Linda University to --CA--.

In the Claims

In column 13 at line 33, In Claim 13, change "are ate." to --aggregate.--.

In column 15 at line 22, In Claim 36, change "are ate" to --aggregate--.

Signed and Sealed this
Fifteenth Day of March, 2016

Michelle K. Lee
*Director of the United States Patent and Trademark Office*